(12) United States Patent
Dahmen et al.

(10) Patent No.: US 7,960,590 B2
(45) Date of Patent: *Jun. 14, 2011

(54) METHOD FOR PRODUCING ETHYLENEAMINES FROM UNTREATED AAN

(75) Inventors: Kirsten Dahmen, Freinsheim (DE); Alfred Oftring, Bad Dürkheim (DE); Randolf Hugo, Dirmstein (DE); Thilo Hahn, Kirchheimbolanden (DE); Katrin Baumann, Mannheim (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/529,101

(22) PCT Filed: Feb. 28, 2008

(86) PCT No.: PCT/EP2008/052405
§ 371 (c)(1), (2), (4) Date: Aug. 28, 2009

(87) PCT Pub. No.: WO2008/104578
PCT Pub. Date: Sep. 4, 2008

(65) Prior Publication Data
US 2010/0121109 A1 May 13, 2010

(30) Foreign Application Priority Data
Mar. 1, 2007 (EP) .................................. 07103288

(51) Int. Cl.
*C07C 209/48* (2006.01)
(52) U.S. Cl. ........................ 564/490; 564/491
(58) Field of Classification Search .................. 564/490, 564/491
See application file for complete search history.

(56) References Cited

U.S. PATENT DOCUMENTS

| | | | |
|---|---|---|---|
| 2,511,487 A | 6/1950 | Thompson | |
| 3,255,248 A | 6/1966 | Suessenguth et al. | |
| 3,988,360 A | 10/1976 | Gaudette et al. | |
| 4,235,821 A | 11/1980 | Butte, Jr. et al. | |
| 4,895,971 A | 1/1990 | Su et al. | |
| 5,079,380 A | 1/1992 | Thunberg | |
| 5,530,127 A | 6/1996 | Reif et al. | |
| 6,297,394 B1 | 10/2001 | Voit et al. | |
| 6,469,211 B2 | 10/2002 | Ansmann et al. | |
| 6,518,449 B1 | 2/2003 | Boschat et al. | |
| 6,852,669 B2 | 2/2005 | Voit et al. | |
| 7,091,153 B2 | 8/2006 | Voit et al. | |

FOREIGN PATENT DOCUMENTS

| | | |
|---|---|---|
| DE | 1154121 | 9/1963 |
| DE | 3003729 A1 | 8/1980 |
| EP | 0212986 A1 | 3/1987 |
| EP | 0382508 A2 | 8/1990 |
| EP | 0426394 A1 | 5/1991 |
| EP | 0696572 A1 | 2/1996 |
| EP | 0963975 A1 | 12/1999 |
| EP | 1209146 A1 | 5/2002 |
| EP | 1742045 A1 | 1/2007 |
| WO | WO-9933561 A1 | 7/1999 |
| WO | WO-9944984 A1 | 9/1999 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,096, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,079, filed Aug. 28, 2009.
U.S. Appl. No. 12/529,087, filed Aug. 28, 2009.
U.S. Appl. No. 12/529,107, filed Aug. 28, 2009.

*Primary Examiner* — Brian J Davis
(74) *Attorney, Agent, or Firm* — Connolly Bove Lodge & Hutz LLP

(57) ABSTRACT

The invention relates to a process for preparing an ethylene amine mixture, which comprises the following steps:
a) crude AAN which is largely free of formaldehyde cyanohydrin (largely FACH-free) is heated at a temperature of from 50 to 150° C. to give an amino nitrile mixture comprising aminoacetonitrile (AAN) and from 5 to 70% by weight of iminodiacetonitrile (DAN),
b) hydrogenation of the amino nitrile mixture obtained in step a) in the presence of a catalyst.
Ethylenediamine (EDA) and/or diethylenetriamine (DETA) and also, if appropriate, further ethylene amines can be isolated from the ethylene amine mixtures obtained.

16 Claims, No Drawings

METHOD FOR PRODUCING ETHYLENEAMINES FROM UNTREATED AAN

CROSS-REFERENCE TO RELATED APPLICATIONS

This application is a national stage application (under 35 U.S.C. §371) of PCT/EP2008/052405, filed Feb. 28, 2008, which claims benefit of European application 07103288.2, filed Mar. 1, 2007.

BACKGROUND OF THE INVENTION

The invention relates to a process for preparing an ethylene amine mixture by hydrogenation of an amino nitrile mixture over a catalyst, in which the amino nitrile mixture is prepared from crude AAN. The individual ethylene amines can, if appropriate, be isolated from the ethylene amine mixture obtained.

It is generally known that nitriles can be hydrogenated in the presence of catalysts to give the corresponding amines. Depending on the reaction parameters chosen, the known processes give the desired products, for example primary amines as main product and secondary and tertiary amines as by-products. A problem here is often that the desired product is obtained with lower selectivity and/or in lower yield, frequently also accompanied by rapid deactivation of the catalyst used.

In addition, it is known that in processes for preparing amines by hydrogenation of nitriles a certain proportion of ammonia improves the selectivity of the hydrogenation to primary amines and suppresses the formation of secondary and tertiary amines. However, hydrogenation in the presence of ammonia involves an additional engineering outlay associated with separation of the ammonia from the product stream, the work-up and possible recirculation of the ammonia. In addition, higher pressures can be required in the hydrogenation, since the partial pressure of the ammonia has to be taken into account.

Thus, ethylenediamine (EDA), which is a starting material for, for example, the synthesis of complexing agents or bleach activators which are used, inter alia, as additives for laundry detergents or cleaners, can be prepared as main product by hydrogenation of aminoacetonitrile (AAN). The hydrogenation of iminodiacetonitrile (IDAN) analogously gives diethylenetriamine (DETA) as main product. However, the hydrogenation of AAN or IDAN also always gives DETA or EDA, respectively, as by-products.

DE-A 3 003 729 describes a process for the hydrogenation of aliphatic nitriles, alkylene oxy nitriles and alkylene amino nitriles to primary amines over a cobalt or ruthenium catalyst in the presence of a solvent system. The solvent system used comprises water and ammonia together with an ether or polyether which preferably has from 4 to 6 carbon atoms and a carbon to oxygen ratio of from 2:1 to 5:1, e.g. dioxane, tetrahydrofuran, methylene glycol dimethyl ether or diethylene glycol dimethyl ether, with cyclic ethers such as dioxane and tetrahydrofuran being particularly preferred. As nitrile component, particular preference is given to dinitriles. However, DE-A 3003 729 does not disclose that compounds having both a cyano group and an amino group in the α position, e.g. AAN, can also be used in the process.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone which comprises the Raney cobalt catalyst in an essentially oxygen-free atmosphere. During the entire reaction time, the polynitrile solution is fed in at a rate which is not greater than the maximum rate at which the polynitrile reacts with the hydrogen in the reaction zone. A reaction parameter K which is suitable for determining the volume feed rate is also mentioned. The process described is restricted to the preparation of polyamines from polynitriles such as iminodiacetonitrile (IDAN), nitrilotriacetonitrile (NATN) or further compounds having 2 or more cyano groups. However, the reaction of compounds having one cyano group, e.g. AAN to EDA, is not described.

EP-A 212 986 relates to a further process in which aliphatic polynitriles can be hydrogenated over a granular Raney cobalt catalyst in the presence of a liquid primary or secondary amine comprised in the feed stream to give the corresponding polyamines. Mention is made of, inter glia, the amino component EDA which always has to be present and also numerous further primary or secondary amines. Furthermore, this document specifically discloses that IDAN can be hydrogenated to DETA.

DE-A 1 154 121 relates to a process for preparing ethylenediamine in which the starting materials hydrocyanic acid, formaldehyde, ammonia and hydrogen are reacted in the presence of a catalyst in a one-pot process. Both the ammonia and the hydrogen are used in a molar excess over the further starting materials hydrocyanic acid and formaldehyde which are present in equimolar amounts. In this process, the AAN formed in situ is thus not isolated but directly reacted further with hydrogen. A disadvantage of this process is that the desired product (EDA) is obtained relatively unselectively in small amounts.

U.S. Pat. No. 3,255,248 describes a process for the hydrogenation of organic nitrogen-carbon compounds, which preferably have amino groups substituted by nitro, N-nitroso, isonitroso or cyano groups or by aromatics, to the corresponding amines in the liquid phase using a sintered catalyst comprising cobalt or nickel. Here, the starting material is sprinkled either alone or in the presence of a solvent, for example water, tetrahydrofuran, methanol, ammonia or the reaction product formed, together with the hydrogen onto the catalyst. If compounds which are unsaturated at the nitrogen atom, e.g. cyano groups, are hydrogenated, the presence of ammonia in the reaction is recommended. This is made clear in Example 1 of this patent, where aminoacetonitrile is sprinkled in the form of an aqueous solution together with liquid ammonia but without another solvent onto the sintered catalyst. The pressure used was 280 atm.

EP-A 1 209 146 relates to a further process for the continuous hydrogenation of nitriles to primary amines, in which the respective nitriles are used in the liquid phase over a suspended, activated Raney catalyst based on an alloy of aluminum and the reaction is carried out in the absence of ammonia and basic alkali metal or alkaline earth metal compounds. Among many others, AAN and IDAN can be used as nitriles in the reaction to form the corresponding ethylene amines. If appropriate, the nitrile to be hydrogenated can also be present in solution in an organic solvent, preferably an alcohol, amine, amide, in particular N-methylpyrrolidone (NMP) and dimethylformamide (DMF), or an ether or ester. However, EP-A 1 209 146 gives no indication that IDAN and AAN can be hydrogenated jointly.

Thus, none of the prior art reports that mixtures of amino nitriles which comprise IDAN and AAN can also be hydrogenated. Rather, the processes of the prior art are restricted to the hydrogenation of individual substances.

Processes for preparing AAN and IDAN are likewise known. Thus, U.S. Pat. No. 5,079,380 relates to a process for preparing AAN, in which ammonia ($NH_3$), formaldehyde (HCHO) and hydrocyanic acid (HCN) are reacted at at least 100° C. It is also generally known that, as an alternative, formaldehyde and hydrocyanic acid can firstly be reacted to form formaldehyde cyanohydrin (FACH) as intermediate which is subsequently reacted with ammonia to give AAN. The molar ratio of ammonia to FACH or to formaldehyde and hydrocyanic acid is usually $\geq 4:1$ [mol/mol]. The temperatures in the AAN synthesis are in the range from 50 to 80° C. and the pH is about 10. To be able to prepare IDAN, ammonia and FACH or ammonia, formaldehyde and hydrocyanic acid are likewise typically used as starting materials. The reaction to form IDAN is generally carried out at higher temperatures (about 100-150° C.), a lower pH of about 5-7 and a smaller proportion of ammonia than in the corresponding synthesis of AAN. Such processes for preparing IDAN are described, for example, in EP-A 426 394 or U.S. Pat. No. 4,895,971. As an alternative, the preparation of IDAN can also be carried out by reaction of urotropin (hexamethylenetetramine; HMTA) with hydrocyanic acid and formaldehyde, as described, for example, in U.S. Pat. No. 3,988,360.

U.S. Pat. No. 2,511,487 relates to a process in which IDAN is prepared from AAN. Here, AAN is mixed with FACH in a molar ratio of about 1:0.3-1.5 [mol/mol] and heated to from 100 to 150° C. in the presence of a mineral acid stabilizer such as phosphoric acid. To obtain a very high yield of IDAN, the reaction preferably takes place at from 135 to 150° C. and for a maximum of 15 minutes. The process described in U.S. Pat. No. 2,511,487 takes place in a conventional flask with cooling facilities.

It is therefore an object of the invention to provide a simple and inexpensive process for preparing the ethylene amines EDA and/or DETA. The process should achieve a high conversion at a high selectivity, with the ratio of DETA to EDA being able to be varied and set specifically.

BRIEF SUMMARY OF THE INVENTION

This object is achieved by a process for preparing an ethylene amine mixture, which comprises the following steps:
a) crude AAN which is largely free of formaldehyde cyanohydrin (largely FACH-free) is heated at a temperature of from 50 to 150° C. to give an amino nitrile mixture comprising aminoacetonitrile (AAN) and from 5 to 70% by weight of iminodiacetonitrile (IDAN),
b) hydrogenation of the amino nitrile mixture obtained in step a) in the presence of a catalyst.

DETAILED DESCRIPTION OF THE INVENTION

The process of the invention has the advantage that the main components of the ethylene amine mixture (EDA and DETA) can be prepared at a high conversion and/or with high selectivity (higher space time yield). The amino nitrile mixture used is preferably reacted completely or virtually completely. This is particularly important in industrial processes since unreacted starting material generally has to be recirculated to the process circuit or be disposed of. Processes in which large amounts of AAN and/or IDAN are not reacted are particularly disadvantageous because of the high instability of AAN and IDAN. Firstly, AAN and also IDAN tends to decompose at relatively high temperatures, so that the decomposition products cannot be recirculated to the respective circuit, and secondly this decomposition can also proceed with explosive vigor. The hydrocyanic acid liberated in the decomposition can also significantly increase the catalyst consumption. Since the amino nitrile mixture can be reacted completely in the process of the invention, no efforts have to be made to recirculate it to the production cycle.

An advantage of the preparation of an ethylene amine mixture instead of the preparation of individual components in separate campaigns or in separate processes is that the addition of ammonia can be dispensed with. In the specific preparation of ethylene amines according to the prior art, ammonia or other additives are generally added to suppress secondary amines. In the synthesis according to the invention of ethylene amine mixtures, suppression of dimerization is not necessary since the dimers are obtained in the product mix and represent products of value. In contrast, in the case of separate syntheses, components obtained in small concentrations cause separation problems and therefore interfere, even if they are products of value. The avoidance of ammonia leads to savings in terms of apparatus as a result of the absence of ammonia separation, storage or recirculation and also possible lower pressures in the hydrogenation reactor due to the intrinsic pressure of ammonia no longer being present. For safety reasons, too, the avoidance of ammonia is advantageous.

Despite the fact that an ethylene amine mixture is obtained in principle in the process of the invention, the main components EDA, DETA and possibly also further ethylene amines obtained as by-products can be obtained by continuous isolation in a single plant. In conventional processes in which the amino nitriles are hydrogenated separately, DETA, EDA and/or further ethylene amines (in each case depending on the starting material used) are in principle always obtained as by-products. Accordingly, the same purification steps as in the process of the invention are generally necessary for separating off the by-products from the respective main product after the individual specific ethylene amine syntheses. Methods of separating off the by-products (DETA or EDA) obtained in the individual processes thus do not differ in principle from methods of isolating the main products (e.g. EDA and DETA) obtained in the process of the invention, only the amount of EDA or DETA to be separated off is different. In addition, in campaign operation, only batchwise operation comes into question, which is impractical because of the desired amounts. In the case of continuous operation, shutdowns and changing over of the plants have to be accepted (reduction in plant availability, cleaning requirements, losses of product, personnel requirements, etc.). Storage capacities corresponding to market requirements also have to be present.

Another advantage is that, depending on market requirements, a higher or lower proportion of EDA or DETA or the further ethylene amines in the ethylene amine mixture can be prepared. The process of the invention is advantageously carried out continuously. This is because the ratio of the starting materials IDAN to AAN is in principle reflected in the ratio of DETA to EDA in the product. Thus, specific amino nitrile mixture compositions can be set in the process of the invention in order to meet the ratio of quantities desired by the market. The process of the invention gives, with high selectivity, an ethylene amine mixture which preferably comprises at least 30% of EDA together with at least 5% of DETA and, if appropriate, further ethylene amines as products of value.

Owing to step a), the process of the invention has the advantage that it is possible to prepare an amino nitrile mixture which comprises defined amounts of the two main constituents AAN and IDAN. A mixture comprising AAN and from 5 to 70% by weight of IDAN can be prepared very selectively. The process of the invention thus enables a variable IDAN content to be set in the amino nitrile mixture. This is achieved in a simple way since only one starting material (AAN) has to be prepared and IDAN is formed from part of this, again within the process of the invention.

In contrast to the process described in U.S. Pat. No. 2,511, 487, in which complete conversion of AAN (by means of FACH) into IDAN is sought, no additional EACH is preferably and advantageously added in the process of the invention. The amino nitrile mixtures having a variable proportion of IDAN can be prepared in this way. A separate preparation of IDAN is likewise unnecessary and the problems associated therewith in the isolation and handling of the product obtained as a solid (IDAN) do not occur in the process of the invention.

A further significant advantage of the process of the invention is that two (main) products (EDA and DETA) can be prepared in variable ratios to one another from only one starting material (crude AAN).

While AAN is a liquid at room temperature (RT), IDAN is solid at room temperature and not readily soluble in customary inert solvents. Owing to the good solubility of the solid amino nitriles in AAN, the handling of solids can be avoided in the process of the invention. For example, IDAN has a solubility of only ~10% in THF at room temperature, while dissolved concentrations of up to ~35% (at 40° C., ~52%) are possible in AAN.

A further advantage is that the amino nitriles can be stored for only a limited time in the crude state under customary conditions (RT) and separate preparation and mixing is therefore impractical.

A further disadvantage of the separate preparation of DETA is the high degree to which it complexes the catalyst. The resulting product inhibition results in a relatively slow hydrogenation rate. In the preparation of EDA, the product inhibition is significantly lower, so that a considerably higher hydrogenation rate of MN is possible, presumably because of lower complexation constants. If the hydrogenation of IDAN is carried out in the presence of at least 30% by weight of MN as in the process of the invention, the product inhibition is reduced. For a given amino nitrile mixture, the space-time yield of the respective components is therefore greater than in the corresponding hydrogenation of the individual components, or the hydrogenation of the mixture can be carried out at significantly lower pressures, which means significantly lower capital costs.

Step a)

As crude AAN, it is generally possible to use any type of AAN in the process of the invention. However, the crude AAN is usually in the form of an aqueous or aqueous-ammoniacal solution. The proportion of AAN in the crude AAN is normally from 5 to 98% by weight, preferably from 10 to 90% by weight. The solvent is not taken into account in the % by weight figures.

The crude AAN is preferably prepared by reaction of an aqueous mixture of ammonia with formaldehyde cyanohydrin (FACH) in a molar ratio of $\geq 4:1$ [mol/mol] at a temperature of from 50 to 80° C. This process is known to those skilled in the art. The reaction is preferably carried out at about 70° C. in a flow reactor at a residence time of about 5-60 minutes, preferably 10-30 minutes. The reaction is preferably carried out so that the proportion of FACH in the crude AAN is very low. For this purpose, a sufficiently long residence time and/or a reaction temperature which is not too low are/is set. If appropriate, these reaction parameters are optimized so that virtually no FACH is present in the output from the reaction.

As an alternative, the crude AAN can be prepared by other methods known to those skilled in the art, for example by reaction of ammonia with formaldehyde and hydrocyanic acid.

For the purposes of the present invention, "largely free of formaldehyde cyanohydrin (largely FACH-free)" means that a maximum of 10 mol % of FACH are present in the crude AAN, based on the amount of AAN. The FACH concentration in the crude AAN is preferably $\leq 1$ mol %, in particular <0.1 mol %, and the crude AAN is particularly preferably completely free of FACH.

Furthermore, it can be advantageous to remove, if appropriate, all or part of the ammonia which has not been reacted in the preparation of the crude AAN from the crude AAN solution. The complete or partial removal of the excess ammonia is preferably carried out by flash evaporation. Preference is given to removing such an amount of ammonia that the molar ratio of ammonia to AAN in the crude AAN is $\leq 2.5:1$ [mol/mol].

Step a) can in principle be carried out in any desired apparatus. For example, step a) of the process of the invention can be carried out in the same apparatus as the preceding synthesis of the crude AAN or step a) is carried out in a separate apparatus. The process of the invention is preferably carried out in the same reactor as the synthesis of the crude AAN.

In continuous operation, it is possible to use, for example, a flow tube or a cascade of flow tubes. Each flow tube can be divided into a plurality of sections in which particular reaction conditions prevail, so that although there is only one apparatus it corresponds in reaction engineering terms to a cascade of flow tubes. This can be achieved in practice by means of different heating or cooling zones, different catalysts or intermediate introduction of reactants or inert components (e.g. solvents). Other reactors can also be used individually or as a cascade. In particular, it is possible to connect different types of reactor or apparatuses to form a cascade. Possible reactor types are, in addition to the flow tube, loop reactors, stirred vessels, falling film evaporators, thin film evaporators or other types of heat exchangers. These apparatuses or reactors can in each case be operated with or without an external circuit which can effect backmixing or simple introduction or removal of heat by means of an external heat exchanger.

In particular, it is possible to carry out the synthesis of the crude ANN in the first reactor or part of a reactor or reactor section. In the second reactor or reactor part or reactor section, complete or partial removal of ammonia can, if appropriate, then be carried out, for example by flashing of the crude AAN stream or by distillation. Finally, the partial transformation of the AAN into IDAN is carried out in a third reactor or in the third section of a reactor or part reactor.

In the case of a batchwise preparation of the reaction mixture, preference is given to using a single reactor or a single apparatus in which the individual steps described (preparation of crude AAN, $NH_3$ removal, partial conversion of AAN into IDAN) are carried out in succession. For this purpose, the reaction conditions desired for the particular substep are set in succession. Suitable types of reactor are, for example, stirred vessels, loop reactors, tank reactors or stirred vessels having a superposed distillation column, in each case with or without an external circuit which serves to regulate the temperature, or all or part of the reaction takes place in an external heat exchanger. In a specific embodiment, reaction and distillation can be combined in a continuous or discontinuous reactive distillation column.

Step a) is preferably carried out in an apparatus selected from among a tube reactor, a flow tube, a falling film evaporator and a thin film evaporator. These reactors can be used individually or as a cascade of identical or different reactors. In particular, a reactor cascade can also be utilized by setting different reaction conditions in different sections of an individual reactor or an individual apparatus.

If appropriate, ammonia liberated in the setting of the desired amino nitrile mixture can also be removed from the apparatus, for example by distilling off $NH_3$. Preference is given to carrying out a simultaneous ammonia removal and synthesis of the amino nitrile mixture in a vessel or stirred vessel having a superposed distillation column or in a reactive distillation column. Furthermore, the molar ratio of ammonia to AAN is preferably set to a value of $\leqq 2.5:1$ [mol/mol].

In the process of the invention, the crude AAN is heated at a temperature of from 50 to 150° C., preferably from 60 to 130° C.

In a further embodiment of the present invention, the crude AAN is prepared in one apparatus and subsequently passed through a separate apparatus (A1). In this alternative embodiment, the crude AAN is heated at a temperature of from 70 to 150° C. The temperature is preferably from 80 to 130° C. The residence time in the apparatus (A1) is preferably not more than 30 minutes. As apparatus (A1), it is in principle possible to use all apparatuses through which the AAN can be passed in the temperature range indicated. The apparatus (A1) is preferably a tube reactor, a flow tube, a falling film evaporator or a thin film evaporator. These types of reactor can be operated individually or be connected to form a cascade. A reactor cascade can also be realized in a single apparatus by setting different reaction conditions in different sections, for example in a flow tube having different temperature zones.

Step a) of the process of the invention can be carried out either as a (semi)batch process or preferably continuously. In an embodiment of the present invention, the preparation of the amino nitrile mixture is carried out directly after the synthesis of the crude AAN. In this embodiment, the crude AAN is preferably prepared by reaction of ammonia with FACH.

In step a) of the process of the invention, it is in principle possible to prepare amino nitrile mixtures comprising MN and from 5 to 70% by weight of IDAN as main components. The proportion of IDAN is preferably from 5 to 50% by weight, more preferably from 10 to 40% by weight, particularly preferably from 10 to 25% by weight. The proportion of AAN is normally from 30 to 95% by weight, preferably from 50 to 95% by weight, particularly preferably from 75 to 90% by weight. The percentages by weight of AAN and IDAN indicated above are based on the total amount of the amino nitriles comprised in the mixture. Any water present, any solvent or other by-products such as further amino nitriles or other impurities are not taken into account in these figures.

To prepare an amino nitrile mixture comprising a very high proportion of IDAN (based on the range from 5 to 70% by weight) in the process of the invention, the following parameters can be altered independently:

i) A relatively high temperature is selected within the indicated temperature range from 70 to 150° C. The higher the temperature selected, the higher the proportion of IDAN in the amino nitrile mixture;

ii) a relatively long time (but generally not more than 30 minutes) for which the crude AAN is heated is selected. The longer the time for which the crude AAN is subjected to an elevated temperature, the higher the proportion of IDAN in the amino nitrile mixture; or iii) the $NH_3$ content in the apparatus is reduced. The lower the $NH_3$ content in the apparatus, the higher the IDAN content in the amino nitrile mixture.

Here, an increase in the temperature promotes the removal of $NH_3$ and thus leads, according to i) and iii), to a higher IDAN content. As the $NH_3$ content decreases, the pressure increases. If appropriate, the temperature can be increased further by increasing the pressure, with the pressure being applied from the outside, or the reaction is carried out under autogenous pressure (=vapor pressure of the mixture at the given temperature).

Step b)

The amino nitrile mixture obtained in step a) is subsequently subjected to a hydrogenation in step b). In the process of the invention, hydrogenation means the reaction of the amino nitrile mixture obtained in step a) with hydrogen in the presence of a hydrogenation catalyst.

The two main components of the amino nitrile mixture are, as indicated above, AAN and IDAN. IDAN is a solid at room temperature, while AAN is a liquid, with IDAN being largely soluble in AAN. In the process of the invention, the amino nitrile mixture obtained in step a) is directly subjected to hydrogenation as a liquid or aqueous solution. Since the amino nitrile mixture can be fed to the hydrogenation as a liquid under the reaction conditions employed in step b) of the process of the invention, it is not absolutely necessary for the hydrogenation of the amino nitrile mixture to be carried out in the presence of a further solvent, such as an organic solvent. However, the additional use of an organic solvent (i.e. an inert organic compound) in step b) is found to be advantageous since stabilization of the individual components of the amino nitrile mixture, in particular in the presence of the resulting amines, can be achieved by, in particular, the use of an organic solvent. In addition, a rinsing effect on the catalyst used can be achieved by the use of solvents, as a result of which its operating life can be increased or its consumption decreased and the space velocity over the catalyst can be improved.

A suitable solvent for step b) which can comprise one or more components should preferably have the following properties:

(a) the solvent should have a stabilizing effect on components of the amino nitrile mixture, in particular reduce decomposition of AAN or IDAN at the prevailing temperatures;

(b) the solvent should have a good dissolution capability for hydrogen;

(c) the solvent should be inert under the reaction conditions;

(d) the reaction mixture (amino nitrile mixture; water from the synthesis and solvent) should form a single phase under the reaction conditions;

(e) the solvent should be selected with a view to a preferred separation of the product from the product stream by distillation after the hydrogenation so as to avoid separations which require a large amount of energy or are complicated in terms of apparatus (e.g. close-boiling mixtures or azeotropes which are difficult to separate);

(f) the solvent should be able to be separated readily from the products, i.e. the boiling point should be sufficiently different from that of the products. Here, a boiling point lower than that of the products is preferred.

Possible solvents are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as ethylene amines, alkylamines, esters such as methyl acetate or ethyl acetate and ethers such as diisopropyl ether, diisobutyl ether, glycol dimethyl ether, diglycol dimethyl ether, dioxane and tetrahydrofuran (THF). Ethers are preferably used in the process of the invention, more preferably cyclic ethers and particularly preferably tetrahydrofuran. In a further preferred embodiment, alcohols, in particular methanol, are used as organic solvent.

Preference is given to mixing the amino nitrile mixture in an amount of from 10 to 90% by weight with the solvent. Based on the particularly preferred solvents methanol and tetrahydrofuran, it is advantageous, for example, to use the amino nitrile mixture in an amount of from 20 to 50% by weight based on the solvent.

The solution used for the preparation of ethylene amines by hydrogenation of the amino nitrile mixture can comprise a proportion of water (from FACH used and water of the reaction) in addition to the amino nitrile mixture and any solvent.

If appropriate, additional additives can be comprised in the solution in which the hydrogenation is carried out. Possible additives are principally hydroxides such as alkali metal hydroxides, alkoxides, amides or amines. Furthermore, acidic additives such as silicates can be additionally comprised in the solution. These substances can be added as pure substance or as a solution in a solvent. The process of the invention is preferably carried out without addition of additives.

In a preferred embodiment of the process, no ammonia is added to the solution in which the hydrogenation is carried out according to step b). If ammonia is still present in the amino nitrile mixture obtained in step a) or is liberated as by-product in the hydrogenation, this does not interfere. Any ammonia present can be removed by methods known to those skilled in the art, for example by distillation.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also Raney catalyst) which are obtained by leaching (activation) of an alloy of hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated by reduction of the metal oxides in a hydrogen-comprising gas stream at elevated temperature either outside the reactor or in the reactor before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. An exception in the activation is the skeletal catalysts which can be activated by leaching with aqueous base, as described in, for example, EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The active catalyst composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO; with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$; for example the catalyst specifically disclosed in this document which has the composition 31.5% by weight of $ZrO_2$, 50% by weight of NiO, 17% by weight of CuO and 1.5% by weight of $MoO_3$. Further suitable catalysts are those described in WO-A-99/44984, which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight based on (a) of a compound based on an alkali metal and/or alkaline earth metal and (d) from 0.001 to 1% by weight based on (a) manganese.

Suspension processes are preferably carried out using Raney catalysts. In the case of Raney catalysts, the active catalyst is produced as "metal sponge" from a binary alloy (nickel, iron, cobalt with aluminum or silicon) by leaching out of one component by means of acid or alkali. Residues of the original alloying component often have a synergistic action.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted with alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air sensitive and pyrophoric and are therefore generally stored and handled under a medium such as water, an organic solvent or a substance which is present in the reaction according to the invention (solvent, starting material, product) or embedded in an organic compound which is solid at room temperature.

According to the invention, preference is given to using a skeletal cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with 1-30% by weight of Al, particularly preferably 2-12% by weight of Al, very particularly preferably 3-6% by weight of Al, 0-10% by weight of Cr, particularly preferably 0.1-7% by weight of Cr, very particularly preferably 0.5-5% by weight of Cr, in particular 1.5-3.5% by weight of Cr, 0-10% by weight of Fe, particularly preferably 0.1-3% by weight of Fe, very particularly preferably 0.2-1% by weight of Fe, and/or 0-10% by weight of Ni, particularly preferably 0.1-7% by weight of Ni, very particularly preferably 0.5-5% by weight of Ni, in particular 1-4% by weight of Ni, with the percentages by weight in each case being based on the total weight of the catalyst.

As catalyst in the process of the invention, use can advantageously be made of, for example, a skeletal cobalt catalyst "Raney 2724" from W.R. Grace & Co. This catalyst has the following composition:

Al: 2-6% by weight, Co: $\geq$86% by weight, Fe: 0-1% by weight, Ni: 1-4% by weight, Cr: 1.5-3.5% by weight.

It is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters for the purposes of the invention.

Such catalysts typically comprise nickel together with 1-30% by weight of Al, particularly preferably 2-20% by weight of Al, very particularly preferably 5-14% by weight of Al, 0-10% by weight of Cr, particularly preferably 0.1-7% by weight of Cr, very particularly preferably 1-4% by weight of Cr, and/or 0-10% by weight of Fe, particularly preferably 0.1-7% by weight of Fe, very particularly preferably 1-4% by weight of Fe, with the percentages by weight in each case being based on the total weight of the catalyst.

As catalyst in the process of the invention, use can advantageously be made of, for example, a skeletal nickel catalyst A 4000 from Johnson Matthey.

This catalyst has the following composition

Al: $\leq$14% by weight, Ni: $\geq$80% by weight, Fe: 1-4% by weight, Cr; 1-4% by weight.

In the case of decreasing activity and/or selectivity of the catalysts, they can be regenerated by methods known to those skilled in the art, as disclosed, for example, in WO 99/33561 and the documents cited therein.

The regeneration of the catalyst can be carried out in the actual reactor (in situ) or on the catalyst which has been removed from the reactor (ex situ). In the case of fixed-bed processes, regeneration is preferably carried out in situ; in the case of suspension processes, part of the catalyst is preferably taken continuously or discontinuously from the reactor, regenerated ex situ and returned.

The temperatures at which the process of the invention is carried out in step b) are in the range from 40 to 150° C., preferably from 70 to 140° C.

The pressure prevailing in the hydrogenation is generally in the range from 5 to 300 bar, preferably from 30 to 250 bar, particularly preferably from 40 to 160 bar.

If appropriate, one or more of the following purification steps i)-iii) can be carried out between step a) and b).

i) Ammonia Flash

Ammonia can be completely or partly separated off from the reaction mixture obtained in step a) by reducing the pressure and/or heating and can, if appropriate after work-up, be recirculated to the AAN synthesis. This can be achieved in one or more stages in an evaporator or a cascade of evaporators, with different pressures or temperatures being able to be set from stage to stage. The removal of ammonia can also be carried out in a distillation column, which is advantageous since HCN which is present in the amino nitrile mixture can also be removed in this way.

ii) Distillation of Water

Water can be completely or partly distilled off either together with the $NH_3$ or, preferably, after the removal of ammonia. This can be achieved in one or more stages in an evaporator or a cascade of evaporators, with different pressures or temperatures being able to be set from stage to stage. The removal of water can also be carried out in a distillation column. The removal of water is preferably carried out under reduced pressure. The remaining amino nitrile mixture can still comprise residues of water and ammonia. A residual water content of at least 10% by weight is preferred. Ammonia is then comprised only in small traces.

iii) Adsorption of Impurities

The amino nitrile mixture obtained in step a) can be purified by adsorption of impurities on an adsorbent, e.g. activated carbon or an ion exchanger, either directly or after removal of ammonia or after removal of water and ammonia. This can be carried out, for example, in an adsorption column packed with the adsorbent.

In a preferred embodiment, the amino nitrile mixture (in step b) is fed to the hydrogenation at a rate which is not greater than the rate at which the amino nitrile mixture reacts with hydrogen in the hydrogenation.

The feed rate is preferably set so that effectively quantitative conversion is achieved. This is influenced by temperature, pressure, type of mixture, amount and type of catalyst and the reaction medium, quality of mixing of the content of the reactor, residence time, etc.

The optimal operating conditions can differ significantly in the hydrogenation of individual amino nitriles. In the hydrogenation according to the invention of an amino nitrile mixture, however, the operating conditions to be set differ only slightly as a function of the composition and can therefore be optimized more easily. Thus, only a small degree of flexibility of the machines and apparatuses used, as is normally provided by standard commercial equipment (e.g. throughput of pumps, operating temperature of heat exchangers, pressure rating of the apparatuses, etc.), is required.

If a solvent is used in step b) of the process of the invention, the solvent can firstly be mixed completely with the amino nitrile mixture. The solution obtained, which can, if appropriate, also comprise water and further additives, is subsequently fed into the reaction vessel comprising the catalyst. If appropriate, for example in the case of semibatch processes, part of the solvent can be initially placed together with the catalyst in the reaction vessel, whereupon the solution is metered in. In the case of continuous processes, part of the solvent can also be introduced into the reaction vessel separately from the solution comprising the amino nitrile mixture, the solvent and, if appropriate, water. Since an AAN/IDAN mixture is used, completely separate introduction of the solvent is also conceivable.

In a preferred embodiment, the AAN/IDAN mixture is fed in as an aqueous or an ammoniacal aqueous solution and the organic solvent is fed in separately.

Step b) of the process of the invention for preparing ethylene amines by hydrogenation of amino nitrile mixtures can be carried out continuously, semicontinuously or batchwise in a fixed-bed, fluidized-bed or suspension mode in customary reaction vessels which are suitable for catalysis. Reaction vessels in which contacting of the amino nitrile mixture and the catalyst with the gaseous hydrogen under pressure is possible are suitable for carrying out the hydrogenation.

The hydrogenation in the suspension mode can be carried out in a stirred reactor, jet loop reactor, jet nozzle reactor, bubble column reactor or in a cascade of identical or different reactors of these types. In the case of hydrogenation over a fixed-bed catalyst, tube reactors but also shell-and-tube reactors are conceivable.

In the case of a fixed-bed catalyst, the amino nitrile mixture is conveyed through the catalyst bed in an upward or downward direction. However, the suspension mode is preferably used in semibatch and preferably continuous operation.

The hydrogenation of the nitrile groups takes place with liberation of heat which generally has to be removed. Heat removal can be effected by means of built-in heat-exchange surfaces, cooling jackets or external heat exchangers in a circuit around the reactor. The hydrogenation reactor or a hydrogenation reactor cascade can be operated in a single pass. As an alternative, a recycle mode of operation in which part of the output from the reactor is recirculated to the reactor inlet, preferably without prior work-up of the recycle stream, is also possible. This enables optimum dilution of the reaction solution to be achieved. In particular, the recycle stream can be cooled in a simple and inexpensive manner by means of an external heat exchanger and the heat of reaction can thus be removed. The reactor can also be operated adiabatically, with the increase in the temperature of the reaction solution being able to be limited by means of the cooled recycle stream. Since the reactor itself then does not have to be cooled, a simple and inexpensive construction is possible. An alternative is a cooled shell-and-tube reactor (only in the case of a fixed bed). A combination of the two modes of operation is also conceivable. Here, preference is given to arranging a fixed-bed reactor downstream of a suspension reactor.

The process of the invention gives an ethylene amine mixture comprising EDA and DETA as main component and further ethylene amines (e.g. piperazine) as secondary components. The ratio of the starting materials AAN and IDAN is in principle reflected after the hydrogenation in the corresponding products EDA and DETA. Depending on the hydrogenation conditions, further DETA can be formed from AAN. The proportion of DETA in the resulting amine mixture, which comprises EDA as main constituent, can increase by 1-10% by weight as a result.

After the hydrogenation, the product obtained (ethylene amine mixture) can be purified further if appropriate, for example by separating off any solvent used, water and/or the catalyst by methods known to those skilled in the art. In particular, the two main products (EDA and DETA) can be isolated together or individually from the ethylene amine mixture by methods known to those skilled in the art. If the two main products are isolated together, for example by distillation, they can subsequently be separated into the two individual products. Pure EDA and pure DETA are thus ultimately obtained. Other impurities, by-products or further ethylene amines can likewise be separated off from the ethylene amine mixture by methods known to those skilled in the art.

In a preferred embodiment, step b) of the process of the invention is carried out using tetrahydrofuran or methanol as solvent. The temperature in the hydrogenation is preferably from 80 to 140° C., and the pressure is preferably from 40 to 160 bar. The hydrogenation is preferably carried out in the absence of ammonia.

A high space velocity over the catalyst, which is a measure of the activity of the catalyst used, is achieved by means of the process of the invention. The space velocity over the catalyst is preferably from 0.3 to 20 mol of nitrile (corresponds to ~0.2 g to 12 g of AAN/g of cat), preferably from 1 to 10 mol of nitrile (~0.5 g-6 g), per gram of catalyst per hour. The higher the space velocity over the catalyst, the higher the space-time yield of ethylene amines can be.

The following examples illustrate the process of the invention. The proportions are given in % by weight, unless indicated otherwise. An internal standard, diethylene glycol dimethyl ether (DEGDME), conveyed with the reaction mixture allows quantification of the product by determination of any volatile decomposition products formed. Quantification is effected by means of gas chromatography (GC), with methanol being added to the samples taken in each case in order to homogenize them.

EXAMPLE 1

Preparation of the Crude AAN

General Method:
Reaction of an aqueous mixture of ammonia with formaldehyde cyanohydrin (FACH) in a molar ratio of $\geq 4:1$ at about 70° C. in a flow reactor. Residence time: about 10 minutes. The crude AAN obtained is largely FACH-free.

The excess ammonia can be partly or completely removed from this mixture by flash evaporation.
Yield of AAN (based on FACH): $\geq 95\%$
Weight ratio of AAN: IDAN=99:1
Selectivity to AAN+IDAN: >97%
Specific Method:
Reaction of 243.4 g (1.742 mol) of 44.5% strength aqueous FACH with 118.6 g (6.96 mol) of liquid ammonia.

The two reactants are mixed by means of a static mixer before entering the tube.

Tube reactor: length=400 mm, diameter=10 mm; with glass sphere packing (diameter=3 mm); volume=60 ml.

After the reaction zone, the product mixture comprises the following approximate composition:
35% of AAN, 20% of ammonia, <1% of FACH, <1% of IDAN, balance: water.

EXAMPLE 2

Step a) of the Process of the Invention

Reaction of the aqueous-ammoniacal AAN solution prepared as described in Example 1 in a flow tube:
Apparatus: as in Example 1
Molar ratio=1:1 (AAN to ammonia): about 28% by weight of AAN, about 9% of ammonia
Molar ratio=1:0.5: about 37% of AAN, about 5-6% of ammonia
Molar ratio=1:1.5: about 25% of AAN, about 10-11% of ammonia Balance: in each case water

| Experiment | Molar ratio of AAN:NH$_3$ | T (° C.) | Res. T. (min.) | Weight ratio (%) of AAN:IDAN |
|---|---|---|---|---|
| 1 | 1:1 | 100 | 20 | 79:21 |
| 2 | 1:1 | 100 | 10 | 87:13 |
| 3 A | 1:0.5 | 100 | 10 | 80:20 |
| 3 B | 1:0.5 | 100 | 20 | 69:31 |
| 4 | 1:1.5 | 120 | 5 | 75:25 |

Res. T. = Residence time in the flow tube
Selectivity (AAN + IDAN): in all cases ≧98%

EXAMPLE 3

Continuous Hydrogenation/30% by Weight of Water 10 g of Cr-doped Raney cobalt are placed in a 270 ml autoclave provided with baffles and disk stirrer and 50 standard l (standard liters)/h of hydrogen are continuously fed in. A mixture of 30 g/h of AAN, 9 g/h of water in 255 g/h of THF is pumped in continuously at 50 bar. Reaction mixture is discharged continuously via an immersed frit. The reaction temperature is maintained at 120° C. The output is depressurized via a regulating valve. Regular samples are analyzed by means of GC. At no time can AAN be detected in the output. The samples show a constant selectivity to EDA of >98% and to DETA of 1%.

6 g/h of the MN are subsequently replaced by 10 g/h of IDAN for 7 hours, i.e. 24 g/h of AAN, 10 g/h of IDAN and 255 g/h of THF are pumped in. Nitrile can no longer be detected in the GC analyses. Here, selectivities to EDA of 66%, to DETA of 30% and to piperazine of 1% are achieved.

For a further 7 hours, 18 g/h of AAN (0.32 mol/h) together with 22.5 g/h of IDAN in 255 g/h of THF including 24 g/h of water are metered in. In this case too, complete conversion of AAN and IDAN occurs. The selectivities of the mixture are 41% of EDA, 51% of DETA and 3% of piperazine.

COMPARATIVE EXAMPLE 4

Continuous Hydrogenation of Crystallized IDAN (Anhydrous)

A) Standard:

10 g of Cr-doped Raney cobalt are placed in a 270 ml autoclave provided with baffles and disk stirrer and 50 standard l/h of hydrogen are continuously fed in. A mixture of 2.9 g/h of IDAN in 60 g/h of THF is pumped in continuously at 180 bar. Reaction mixture is discharged continuously via an immersed frit. The reaction temperature is maintained at 120° C. The output is depressurized via a regulating valve. Regular samples are analyzed by means of GC. No IDAN can be detected during the 140 hour duration of the experiment. The selectivities are 0.5% of EDA, 90% of DETA and 4% of piperazine.

B) Higher Space Velocity Over the Catalyst 6 g of Cr-doped Raney cobalt are placed in a 270 ml autoclave provided with baffles and disk stirrer and 50 standard l/h of hydrogen are continuously fed in. A mixture of 7.5 g/h of IDAN in 140 g/h of THF is pumped in continuously at 170 bar. Reaction mixture is discharged continuously via a cover frit. The reaction temperature is maintained at 120° C. The output is depressurized via a regulating valve. Regular samples are analyzed by means of GC. After 9 hours, 4% of IDAN can be detected. The selectivity to DETA is only 68%. After 24 hours, only 16% of DETA and a conversion of 40% can be detected.

The above examples show that the IDAN present in the amino nitrile mixture can be hydrogenated significantly more quickly in the process of the invention than in processes according to the prior art (comparative examples). Despite the presence of AAN, it is thus possible to hydrogenate 30 times the amount of IDAN per hour compared to the conventional IDAN hydrogenation. Furthermore, it is found that IDAN can also be hydrogenated at much lower pressures. This is advantageous in terms of the equipment used; in addition, the process of the invention can be carried out in the same apparatus as the conventional individual hydrogenation of AAN to EDA.

The invention claimed is:

1. A process for preparing an ethylene amine mixture, which comprises the following steps:
    a) heating crude AAN which is largely free of formaldehyde cyanohydrin (largely FACH-free) at a temperature of from 50 to 150° C. to give an amino nitrile mixture comprising aminoacetonitrile (AAN) and from 5 to 70% by weight of iminodiacetonitrile (IDAN),
    b) hydrogenation of the amino nitrile mixture obtained in step a) in the presence of a catalyst.

2. The process according to claim 1, wherein the catalyst used in step b) is a Raney catalyst.

3. The process according to claim 2, wherein the Raney catalyst is a Raney nickel catalyst or a Raney cobalt catalyst.

4. The process according to claim 1, wherein the hydrogenation is carried out in the presence of water or an organic solvent.

5. The process according to claim 4, wherein the solvent is tetrahydrofuran or methanol.

6. The process according to claim 1, wherein the pressure is from 40 to 160 bar or the temperature is from 80° C. to 140° C. in step b).

7. The process according to claim 1, wherein the amino nitrile mixture comprises from 10 to 40% by weight of IDAN.

8. The process according to claim 1, wherein ethylenediamine (EDA) and diethylenetriamine (DETA) and optionally further ethylene amines are isolated from the ethylene amine mixture after the hydrogenation.

9. The process according to claim 1, wherein the amino nitrile mixture is fed to the hydrogenation in step b) at a rate which is not greater than the rate at which the amino nitrile mixture reacts with hydrogen in the hydrogenation.

10. The process according to claim 1, wherein the hydrogenation is carried out without addition of ammonia in step b).

11. The process according to claim 1, wherein crude AAN is heated at a temperature of 60-130° C. in step a).

12. The process according to claim 1, wherein step a) is carried out in a tube reactor, flow tube, falling film evaporator, thin film evaporator or a cascade of two or more of the types of reactor mentioned, with a cascade being able to comprise reactors of the same type or of different types.

13. The process according to claim 1, wherein, in step a), the molar ratio of $NH_3$ to AAN in the crude AAN is $\leq 2.5:1$ [mol/mol] or $NH_3$ liberated during the setting of the amino nitrile mixture is distilled off from the apparatus.

14. The process according to claim 1, wherein the crude AAN is prepared from $NH_3$ and formaldehyde cyanohydrin (FACH) in a molar ratio of $\geq 4:1$ [mol/mol] and at a temperature of from 50 to 80° C.

15. The process according to claim 1, wherein step b) is carried out directly after step a).

16. The process according to claim 1, wherein an ammonia flash, a distillation of water or an absorption of impurities is carried out between step a) and step b).

* * * * *